United States Patent
Leonidov

(12) 
(10) Patent No.: US 6,538,001 B1
(45) Date of Patent: Mar. 25, 2003

(54) CRYSTALLINE MODIFICATION OF 5-FLUORO-1-(TETRAHYDRO-2-FURYL) URACIL AND COMPLEX COMPOUNDS BASED THEREON, PRODUCING ANTINEOPLASTIC EFFECT

(76) Inventor: Nikolai Borisovich Leonidov, Russian Federation, Moscow, ulitsa Zatonnaya, 12, korpus 1, kv.158 (RU)

( * ) Notice: Subject to any disclaimer, the term of this patent is extended or adjusted under 35 U.S.C. 154(b) by 0 days.

(21) Appl. No.: 09/807,652
(22) PCT Filed: Oct. 12, 1998
(86) PCT No.: PCT/RU98/00319
§ 371 (c)(1),
(2), (4) Date: Apr. 12, 2001
(87) PCT Pub. No.: WO00/21956
PCT Pub. Date: Apr. 20, 2000
(51) Int. Cl.[7] .................... A61K 31/505; C07D 419/00
(52) U.S. Cl. .................. 514/269; 514/274; 544/310; 544/313
(58) Field of Search ................... 514/269, 274; 544/310, 313

(56) References Cited

PUBLICATIONS

Amagai et. al., Bull. Chem. Soc. Jpn., vol. 62, No. 4, pp. 1078–1080, 1989.*
Uchida et. al., Chem. Pharm. Bull., vol. 41, No. 9, pp. 1632–1635, 1993.*

* cited by examiner

Primary Examiner—Mukund J. Shah
Assistant Examiner—Tamthom N. Truong
(74) Attorney, Agent, or Firm—Abelman, Frayne & Schwab

(57) ABSTRACT

The invention relates to a novel, heretofore unknown polymorphous modification of 5-fluoro-1-(tetrahydro-2-furyl) uracil (tegafur) having antineoplastic activity. This form is crystalline, and its characteristics it differs essentially from the modification known earlier. In particular, it has an enhanced specific activity. The new form is physically stable and may find application in medicine for treating oncological patients. New anticancer medicinal substances prepared in the form of stable molecular complexes on the basis of said new modification, in particular, crystalline complexes with 6-methyluracil, and amorphous complexes with the biologically active substances from licorice, are also described.

14 Claims, 14 Drawing Sheets

CRYSTALLINE MODIFICATION OF 5-FLUORO-1-(TETRAHYDRO-2-FURYL) URACIL AND COMPLEX COMPOUNDS BASED THEREON, PRODUCING ANTINEOPLASTIC EFFECT

FIELD OF THE ART

The present invention relates to the field of oncology, particularly to polymorphous modifications of anticancer drugs and to complex compounds producing a synergistic antineoplastic effect. The subject of the invention is a new physically stable crystalline modification of ftorafur (INN, tegafur), namely, of 5-fluoro-1-(tetrahydro-2-furyl)uracil, which has an enhanced antineoplastic activity, compared with the modifications known heretofore, as well as new anticancer drugs based thereon, in the form of stable molecular complexes.

PRIOR ART

There is known a large number of medicinal substances and their combinations that are the result of comprehensive investigations of and improvements in antineoplastic substances. Chemotherapeutic substances effective with respect to malignant neoplasms are used in clinical practice. Though the results of such therapy have been improved substantially in recent years, it should be noted that in many cases the efficiency remains insignificant or insufficient for attaining the required degree of inhibiting the tumor growth and an essential extension of the life span of patients. Furthermore, most of the antineoplastic preparations are characterized by high toxicity, and this tells negatively on the process of treatment.

Ftorafur, 5-fluoro-1-(tetrahydro-2-furyl)uracil (INN, tegafur), synthesized by S. A. Giller with coworkers (U.S. Pat. No. 1,168,391) as a precursor of 5-fluorouracil (hereinafter referred to as 5FU) is an effective antineoplastic preparation and is widely used in treating various tumors, particularly, of the gastrointestinal tract and of the mammary gland.

Since tegafur is a sufficiently toxic compound, numerous attempts were made to reduce its toxicity and/or increase its effectiveness.

Pharmacopeial tegafur (corresponding to FS 42-1182-86) is characterized in the x-ray powder diffraction pattern by the following interplanar distances d and the relative intensity of reflections I:

| d, Å | I |
| --- | --- |
| 8.917 | 64 |
| 7.199 | 13 |
| 6.102 | 14 |
| 5.808 | 69 |
| 5.388 | 25 |
| 4.845 | 43 |
| 4.677 | 90 |
| 4.522 | 100 |
| 4.139 | 13 |
| 4.085 | 48 |
| 4.013 | 24 |
| 3.949 | 48 |
| 3.715 | 17 |
| 3.620 | 26 |
| 3.572 | 75 |
| 3.450 | 86 |
| 3.248 | 32 |
| 3.131 | 84 |
| 2.907 | 25 |
| 2.842 | 17 |
| 2.798 | 34 |
| 2.328 | 17 |
| 2.308 | 15 |
| 2.171 | 19 |
| 1.748 | 71 |

The differential scanning calorimetry (DSC) curve of the pharmacopeial tegafur, shown in FIG. 7, displays two endothermal effects. The first, broad effect is in the range of 84.8–128.1° C.; the second, melting effect is in the range of 172.3–192.0° C. The UV spectrum is shown in FIG. 11.

In particular, over many years attempts have been made to modernize the very molecule of tegafur. For instance, in Belgian Patent No. 855121 there are described optically active isomers of 2'R- and 2'S-tegafur which is chemically a racemate. However, investigations carried out by different groups of scientists (for instance, by Yasumoto M. et al., "J. Med. Chem.", 1977, vol. 20, No. 12, 1592–1594 or by Horwitz J. P. et al., "Cancer Res.", 1975, vol. 35, 1301–1304) showed that the biological activity of both isomers is practically the same and does not differ from the activity of the racemate. The toxicity of one or another isomer does not display substantial differences from the initial substance either.

Furthermore, four crystalline forms of tegafur were produced and investigated (Uchida T. et al., "Chem. Pharm. Bull.", vol. 41, No. 9, 1632–1635). After treating the initial tegafur (corresponding to JP XII), α-, β-, γ-, and δ-modifications were isolated. These crystalline modifications differ in their x-ray powder diffraction patterns, IR spectra, and DSC curves. For producing an α-form, tegafur was dissolved in warm acetone and allowed to crystallize at room temperature. Colorless columnar crystals were separated by filtration. Colorless prismatic crystals of the β-form were prepared from a saturated methanol solution by evaporating the solvent with the help of a rotary evaporator. Crystals of the γ-form were obtained by heating the βform at 130° C. for 1 hour. Crystals of the δ-form were isolated by recrystallization from a methanol solution (very slow evaporation of methanol) at room temperature. None of the above-cited modifications offers essential therapeutic advantages.

From the above-stated a conclusion can be drawn that the problem of enhancing the tegafur activity by the synthesis or isomers or producing polymorphous modifications is still unsolved.

Concurrently, searches for compositions—synergistic mixtures containing tegafur as the active substance—were carried out.

The discovery of a combination of medicinal substances, consisting of tegafur and uracil, was preceded by an idea that since 5-FU becomes metabolized too rapidly and loses activity in the organism, uracil may be used for inhibiting these processes (U.S. Pat. No. 5,534,513). It turned out that uracil as such does not display an antineoplastic activity, it has the property to potentiate the antineoplastic effect. An investigation of the effectiveness of a mixture of tegafur and uracil (tegafur:uracil molar ratio of 1:4) is discussed, e.g., in the work of Kagawa Y. et al., "Cancer Investigation", 1955, vol. 13, No. 5, 470–474.

Furthermore, there was produced and investigated a composition containing tegafur, uracil and folic acid (Sanchiz F. and Milla A., "Jpn. Journal Clin. Oncol.", 1994, vol. 24, No. 6, 322–326).

In such combination preparations an aspect of extreme importance is an optimal dosage of both the active component and of the substance potentiating the activity. It is desirable that the potentiating substance should be used in minimal doses (for reducing its own toxic effect) or that this substance per se should practically have no toxic effect. Presently known synergistic preparations containing tegafur, as the active component, and a potentiator are not always optimized with respect to both the qualitative and quantitative formulation of the components. For instance, uracil (which is usually used for potentiating the activity of tegafur) is a toxic compound, though its toxicity is less pronounced compared with other substances capable of potentiating the action of tegafur:thymine, thymine, thymidine or uridine (Fujita H., Experimental and Clinical Pharmacotherapy, Issue 12, Riga, 1983, p. 205).

Hence, the present-day therapy of neoplasms requires improved preparations used in oncology, as well as developing medicinal preparations displaying high antineoplastic activity along with minimized toxicity.

DISCLOSURE OF THE INVENTION

It is an object of the present invention to provide physically stable form of tegafur having an enhanced pharmacological activity. As a result of experiments it was unexpectedly found that an enhanced specific activity along with physical stability during a long period of time sufficient for commercial use is displayed by a hitherto-unknown metastable modification of tegafur, hereafter referred to as form V.

A novel form V comprises a light, "airy" white powder.

Form V is characterized in the x-ray powder diffraction pattern by the following interplanar distances d and the relative intensity of reflections I:

| d, Å | I |
|---|---|
| 9.035 | 63 |
| 7.237 | 23 |
| 6.149 | 19 |
| 5.839 | 100 |
| 5.413 | 17 |
| 4.704 | 42 |
| 4.551 | 62 |
| 4.104 | 36 |
| 4.041 | 28 |
| 3.966 | 25 |
| 3.730 | 20 |
| 3.626 | 25 |
| 3.588 | 42 |
| 3.473 | 60 |
| 3.437 | 50 |
| 3.255 | 30 |
| 3.143 | 36 |
| 2.915 | 23 |
| 2.382 | 16 |
| 2.336 | 20 |

The carried out thermal analysis revealed in the novel form three pronounced peaks on the DSC curve.

The first peak is a transition of α→β type in the region of 96.6–102° C. The second and third peaks are a superposition of two endothermal effects: a β→γ transition in the range of 157.1–174.2° C. and an effect of melting of the γ-form with the maximum temperature of 174° C. superposed thereonto. The point of superposition of the second and third effects is in the neighborhood of 167.6° C.

The UV spectrum of form V is shown in FIG. 10.

Form V of tegafur is prepared by dissolving a pharmacopeial tegafur substance or its individual polymorphous modifications in water, alcohol, or an alcoholic-aqueous mixture. The solvent should preferably be preheated to 40–65° C. After that the resulting solution is introduced into a container with an anti-solvent (e.g., dimethyl ether, diethyl ether or chloroform) preliminarily cooled down to a temperature of at least 10° C. The resulting precipitate is separated, the residues of the solvents are removed, and a crystalline powder of form V is obtained.

The novel crystalline modification of tegafur is physically stable and does not lose its properties on blending with pharmaceutically acceptable carriers or fillers, which makes this modification suitable for use in medicinal preparations. However, unexpectedly it was found that said form V has the property of forming completes with some organic molecules, including those having biological activity. In particular, complex compounds were obtained with 2,4-dioxo-6-methyl-1,2,3,-tetrahydropyrimidine (hereafter referred to as methyluracil) and with biologically active vegetable extracts produced, in particular from licorice (Radices Glycyrrhizae).

Complex compounds can be produced under definite technological conditions, leading to the formation of non-valence bonds between the molecules of tegafur and the molecules of organic compounds which enter into the interactions of such kind with tegafur.

There are three possible ways of synthesizing complex compounds. The first way envisages a single-step transfer of a physical mixture of tegafur and other organic molecules which are planned to be included in the composition of a complex into a high-energy (metastable) state. It was found that under these conditions tegafur passes into form V which is capable to form stable molecular complexes.

A physical mixture can be transferred into a high-energy state by different methods, the only condition in their carrying out being that they should yield form V of tegafur. Such methods can be, for example, joint micronization (particularly, milling) or other known methods affecting the energy of a molecule.

The second way of producing complexes consists in blending a preliminarily prepared form V of tegafur with other components of the complex: an individual compound or a mixture of compounds which at the moment of blending are in a thermodynamically stable state.

The third way of producing complexes consists in blending a preliminarily prepared form V of tegafur with the second component of the complex, this second component already being in the high-energy state.

For producing complexes, it is possible to use, in particular: methyluracil (M. D. Mashkovskii, Drugs, 1997, Kharkov, vol. 2, p. 168 (in Russian)), β-form of methyluracil (hereafter referred to as Betamecil) having a reduced toxicity (U.S. Pat. No. 5,543,147), different licorice extracts, e.g., Extractum Glycyrrhizae siccum (M. D. Mashkovskii, Drugs, 1997, Kharkov, vol. 1, pp. 345–346 (in Russian)).

The molecular complex tegafur-methyluracil in the molar ratio of 1:2 (complex compound 1a) is a white fine-crystalline powder, and it is characterized in the x-ray powder diffraction pattern by the following interplanar distances d and the relative intensity of reflections I:

| d, Å   | I   |
|--------|-----|
| 9.090  | 19  |
| 7.234  | 32  |
| 6.883  | 100 |
| 5.864  | 13  |
| 4.831  | 27  |
| 4.571  | 13  |
| 4.197  | 25  |
| 3.627  | 15  |
| 3.448  | 18  |
| 3.254  | 26  |
| 3.192  | 13  |
| 3.149  | 6   |
| 2.933  | 13  |
| 2.448  | 8   |
| 2.300  | 8   |

The DSC curve of compound 1a is shown in FIG. 8. The curve displays two endothermal effects. The first effect of α→β type is in the range of 117.1–132° C. The second effect of melting of β-form is in the range of 149.9–167.1° C.

The UV spectrum of compound 1a, characterizing the individuality of this substance, is shown in FIG. 12.

The molecular complex tegafur-methyluracil in the molar ratio of 1:1 (complex compound 1b) is a white fine-crystalline powder, and it is characterized in the x-ray powder diffraction pattern by the following interplanar distances d and the relative intensity of reflections I:

| d, Å  | I   |
|-------|-----|
| 7.187 | 53  |
| 6.841 | 100 |
| 4.806 | 41  |
| 4.181 | 37  |
| 3.669 | 20  |
| 3.474 | 21  |

The complex tegafur-licorice (complex compound 2) is amorphous in terms of x-ray diffraction pattern analysis and comprises a light clumping yellow powder with a brownish hue.

The DSC curve of compound 2, shown in FIG. 9, displays e combination of two endothermal effects: a broad effect lies in the range of 98.2–125.0° C.; the second effect, accompanied by decomposition of the substance, lies in the range of 125.0–171.5° C.

The UV spectrum of compound 2, which supports the individuality of this substance, is shown in FIG. 13.

Form V excels in solubility the hitherto-known modifications of tegafur. Moreover, the novel form of tegafur, compared with the hitherto-known polymorphous modifications thereof, has an enhanced specific activity. Complex compounds display a still greater specific activity (compared not only with pharmacopeial tegafur, but also with novel form V), i.e., there takes place potentiation of the pharmacological effect.

The obtained novel crystalline modification of ftorafur and complex compounds based on this modification may find extensive application in medicine for treating oncological diseases. This will make it possible to broaden the range of medicaments acting on tumor cells and, correspondingly, to increase the effectiveness of treating patients suffering from malignant neoplasms.

BEST MODE OF CARRYING OUT THE INVENTION

1. Preparing Form V of Tegafur

Figure 1:
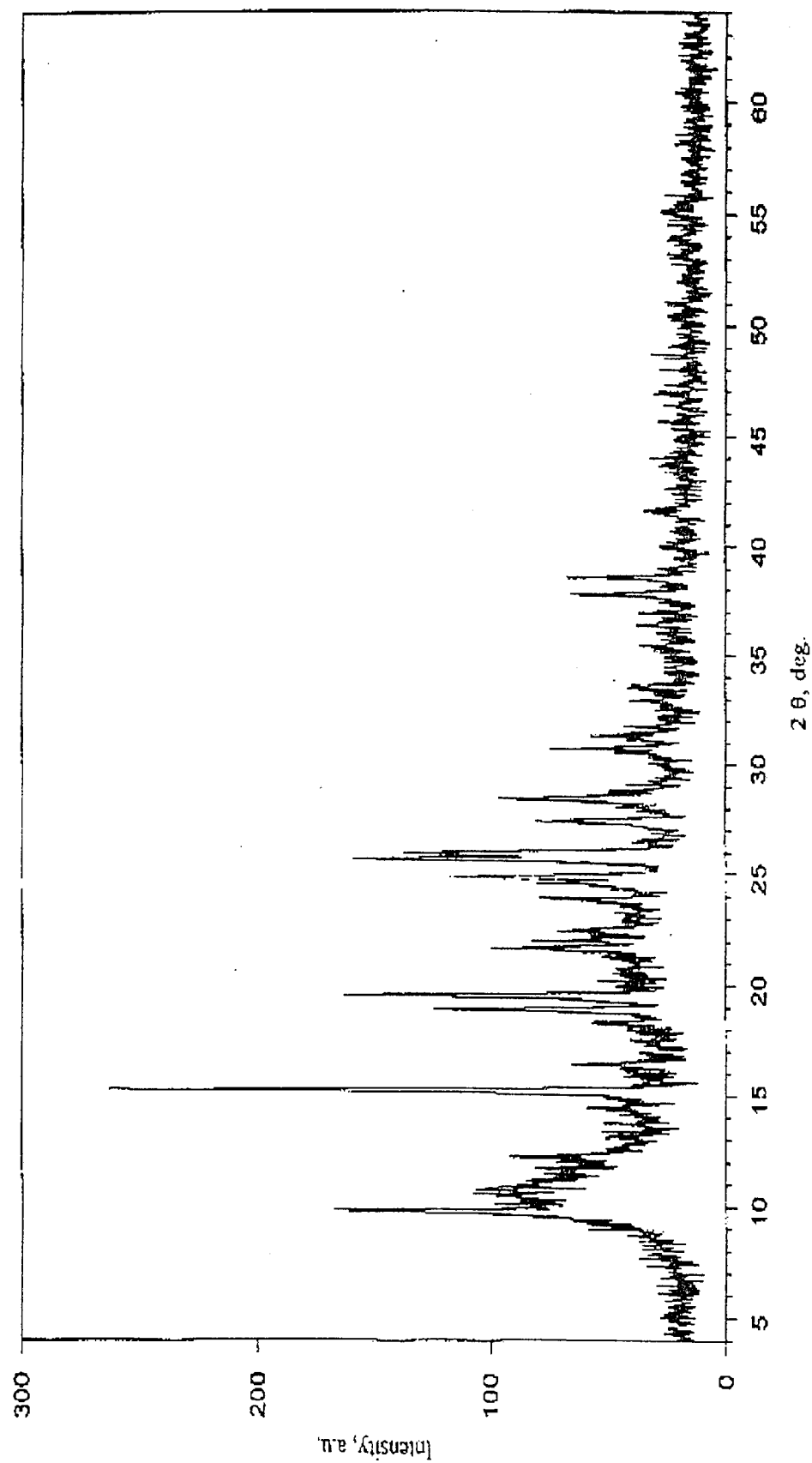
FIG. 1 shows an x-ray powder diffraction pattern of the claimed form V of tegafur.
Figure 2:
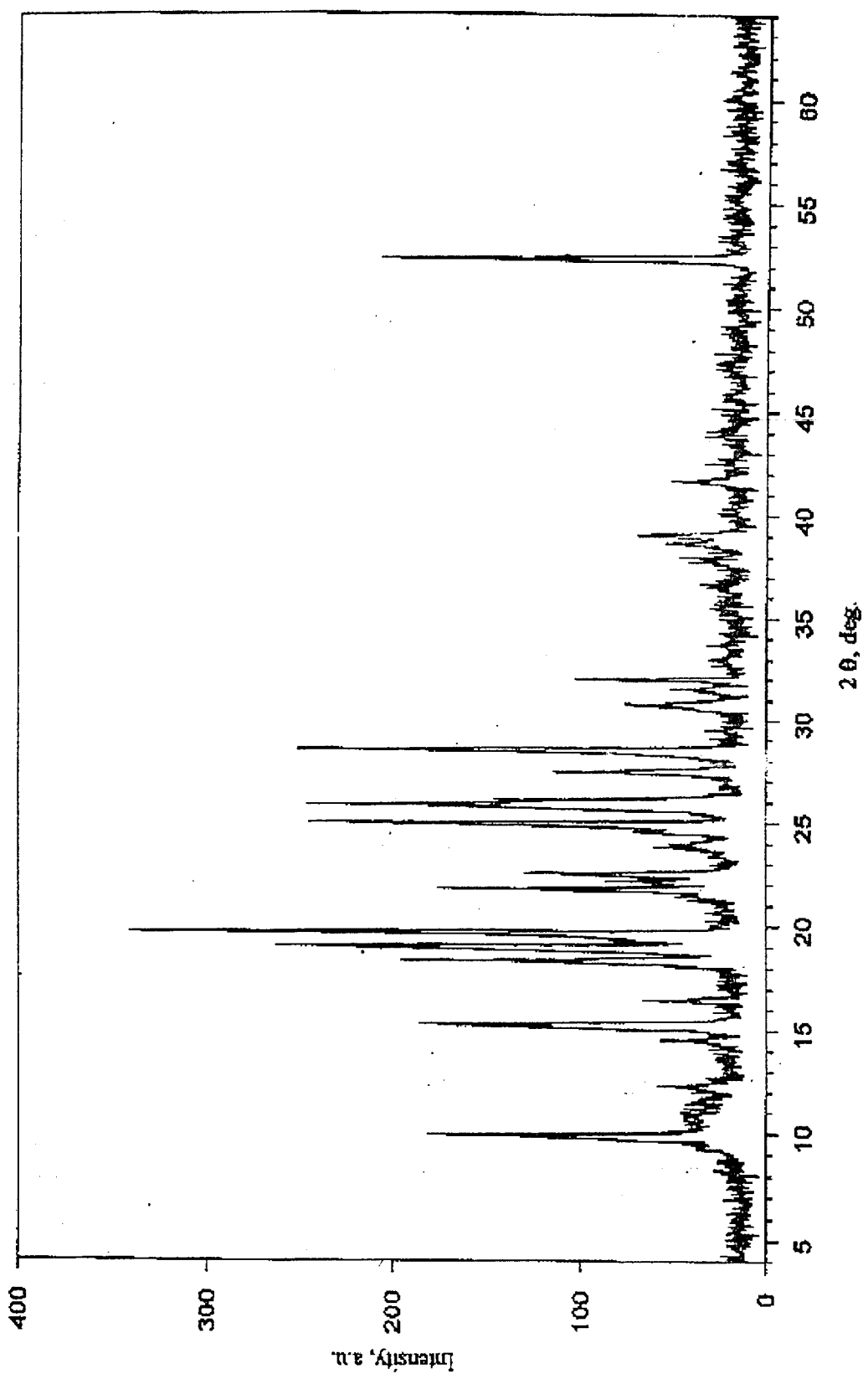
FIG. 2 shows an x-ray powder diffraction pattern of pharmacopeial tegafur.
Figure 3:
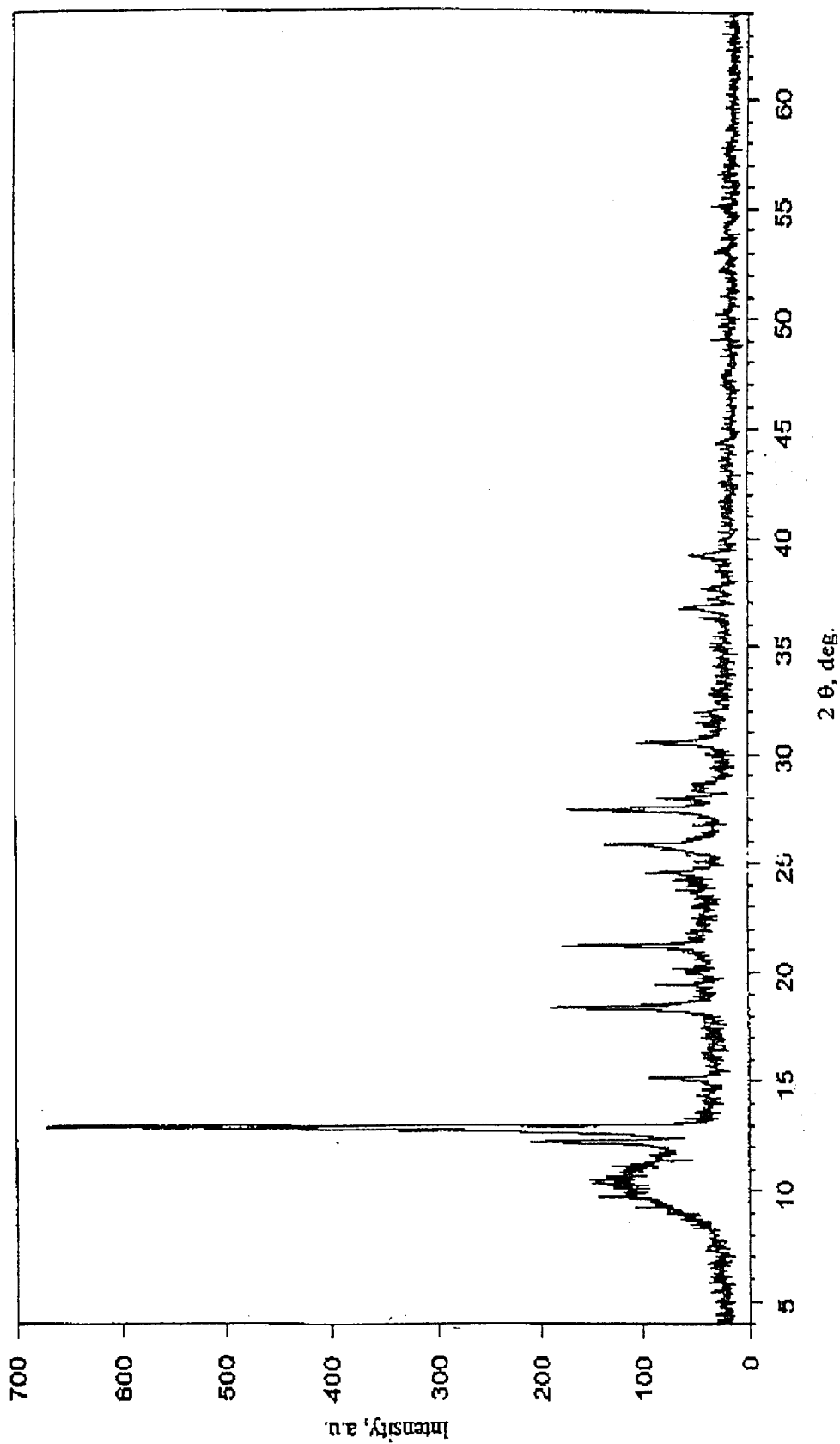
FIG. 3 shows an x-ray powder diffraction pattern of the molecular complex tegafur-methyluracil in the ratio of 1:2.
Figure 4:
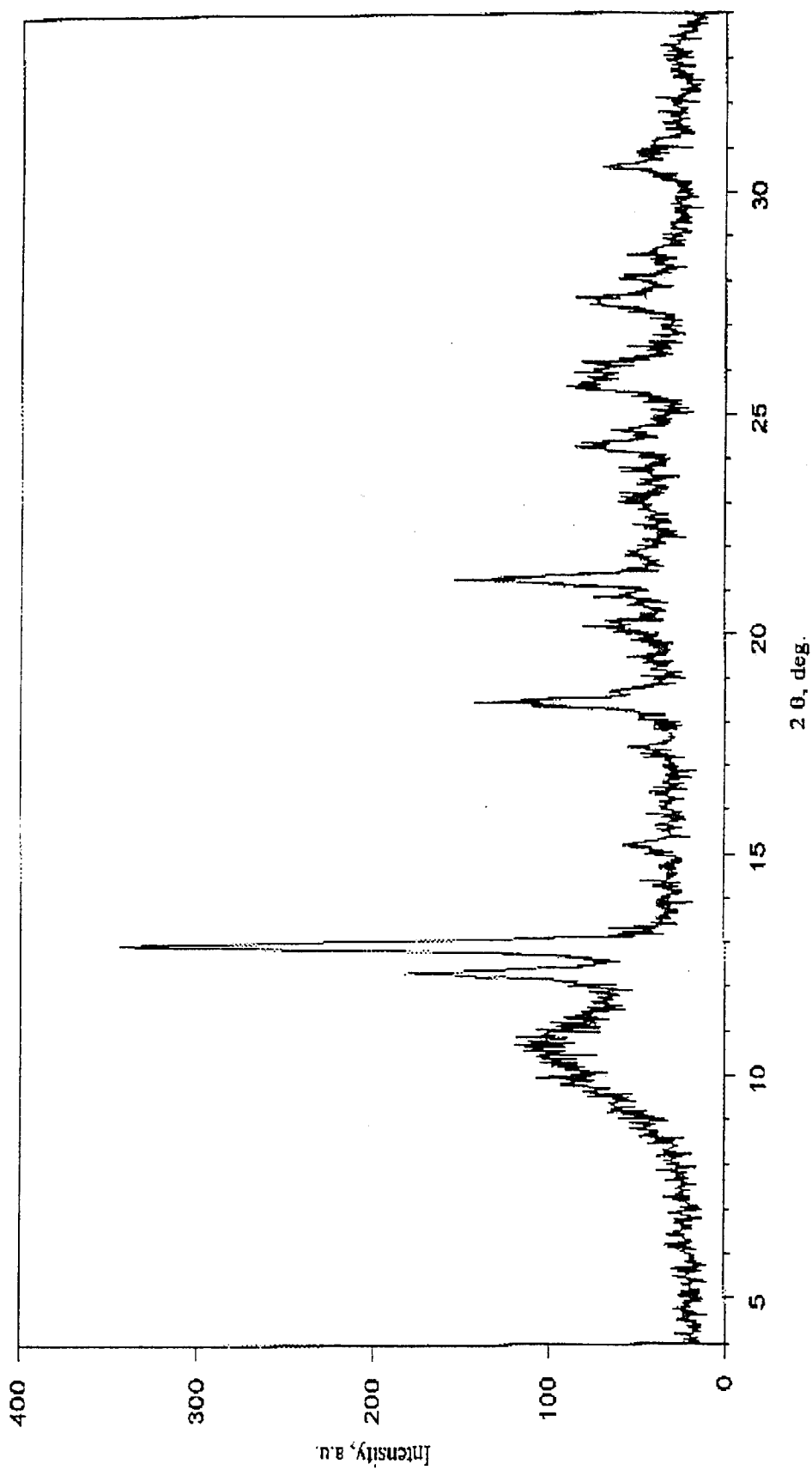
FIG. 4 shows an x-ray powder diffraction pattern of the molecular complex tegafur-methyluracil in the ratio of 1:1.
Figure 5:
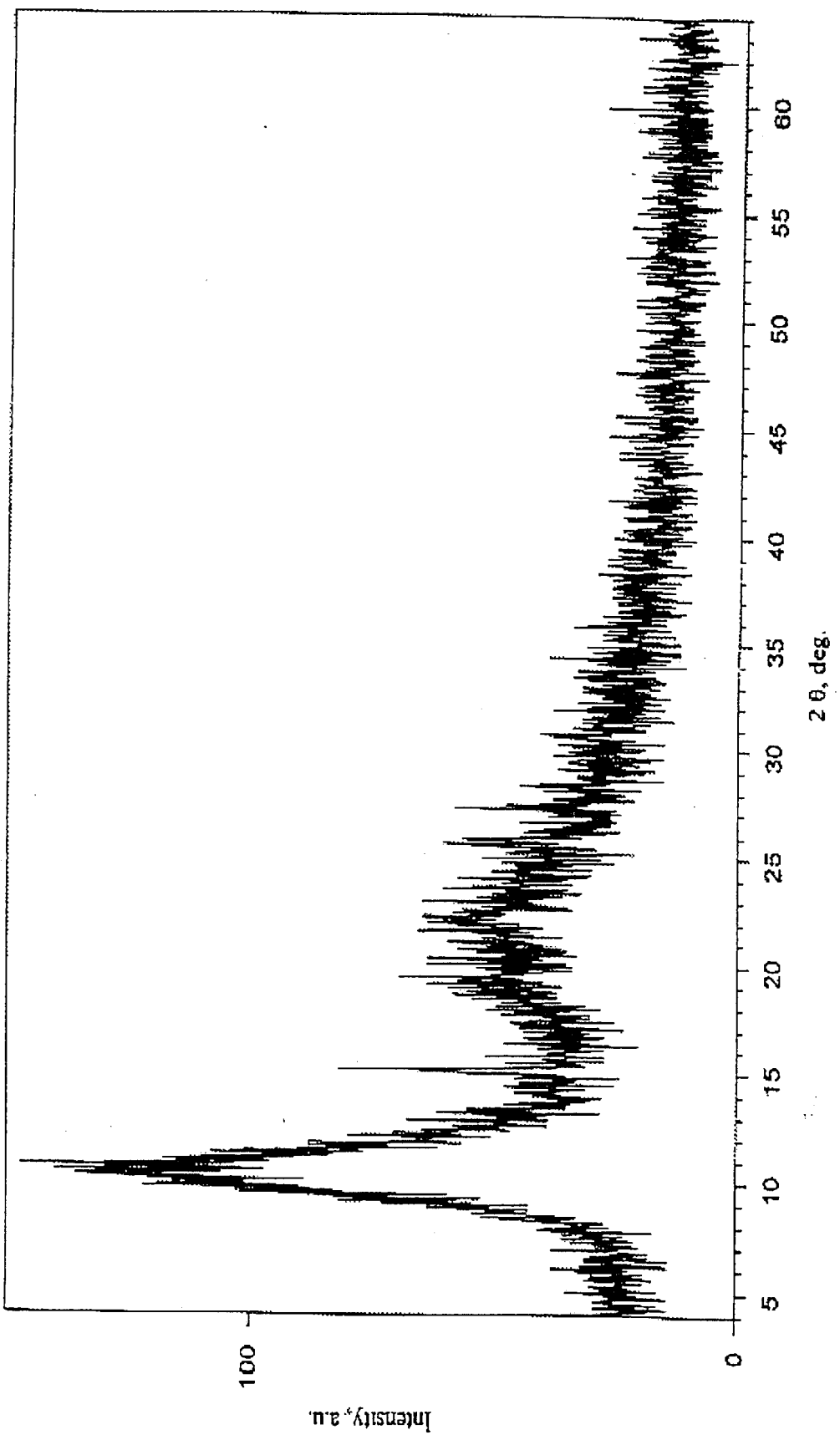
FIG. 5 shows an x-ray powder diffraction pattern of the complex compound tegafur-licorice.
Figure 6:
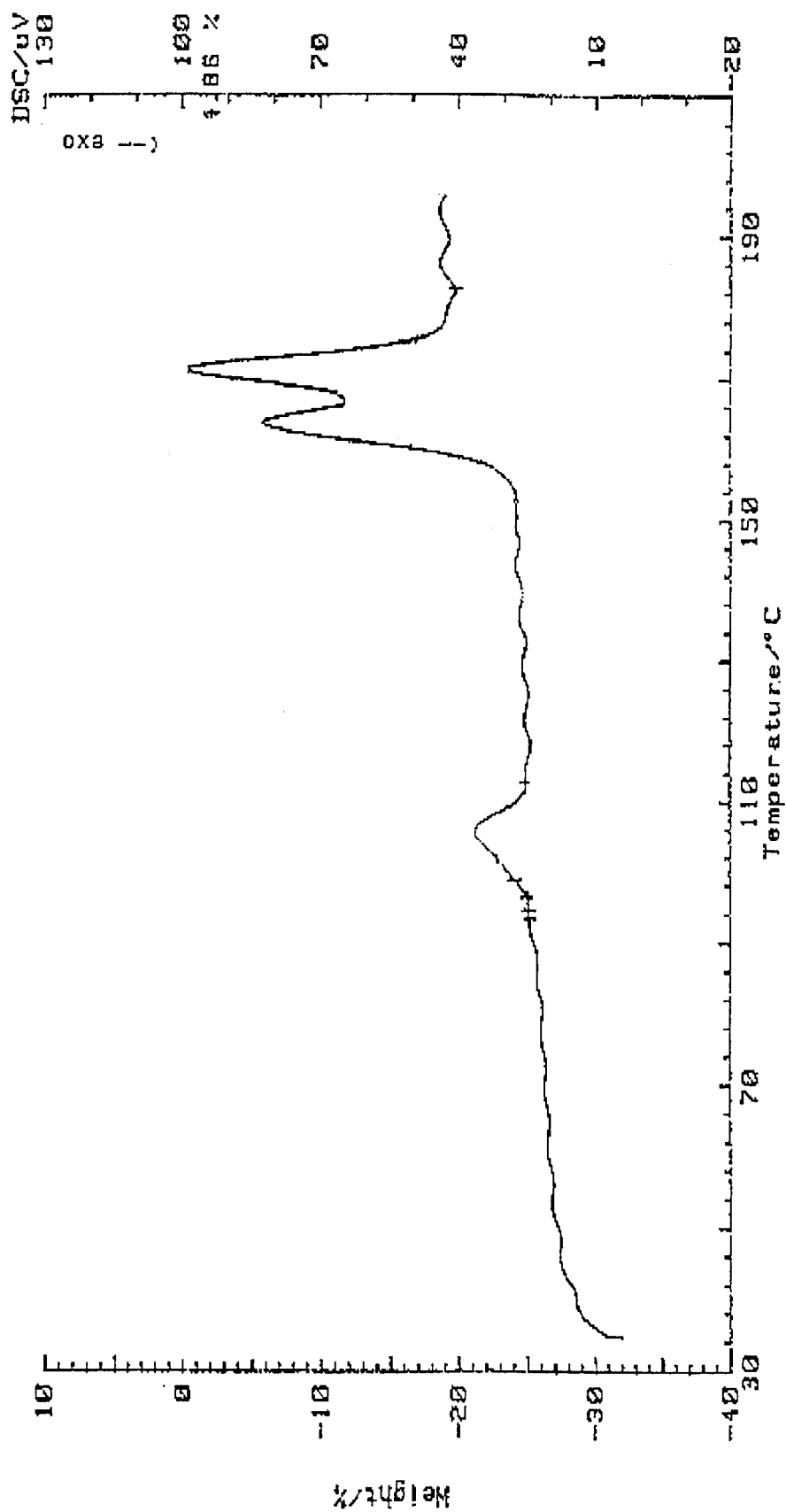
FIG. 6 shows a DSC curve of the claimed form V of tegafur.
Figure 7:
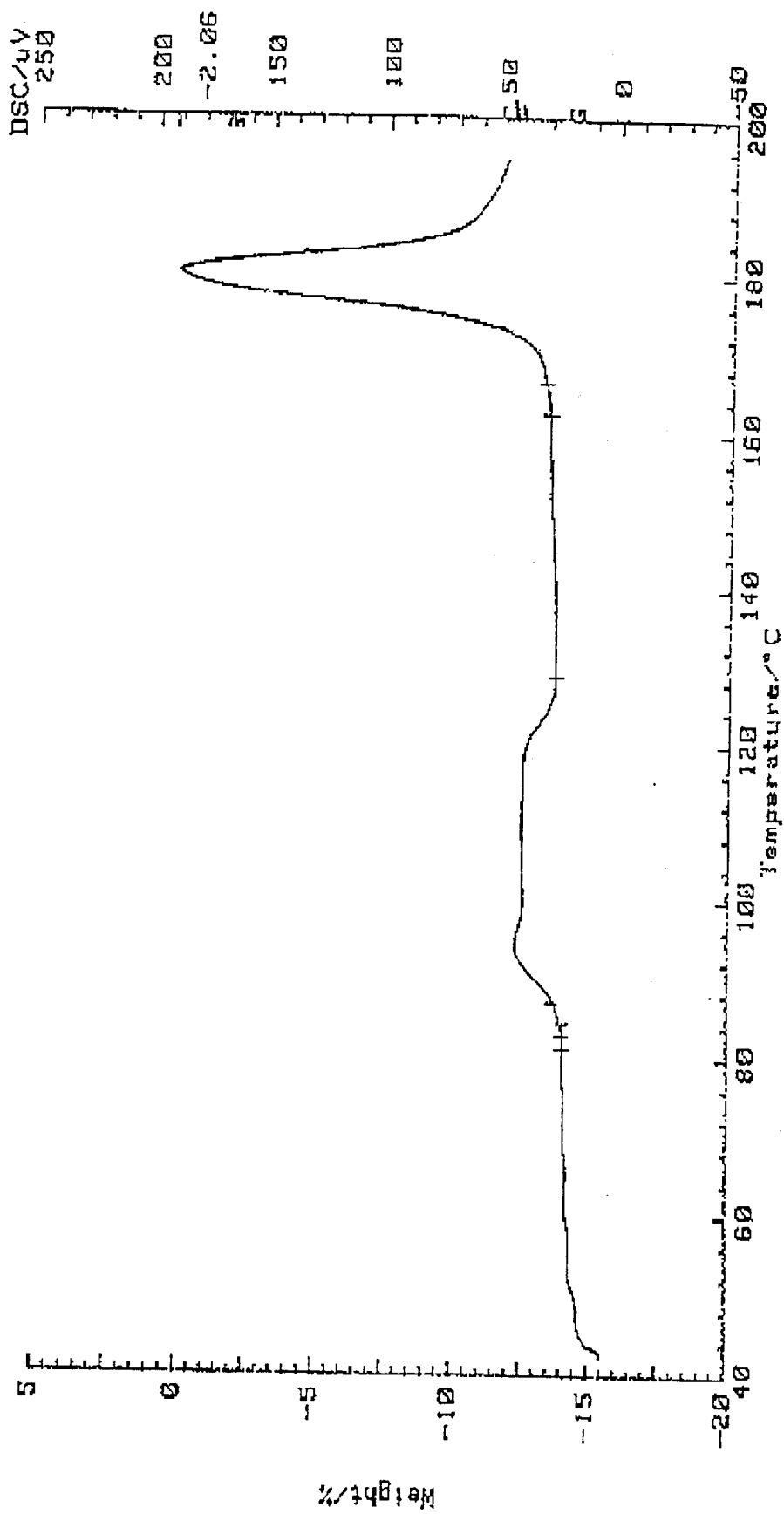
FIG. 7 shows a DSC curve of pharmacopeial tegafur.
Figure 8:
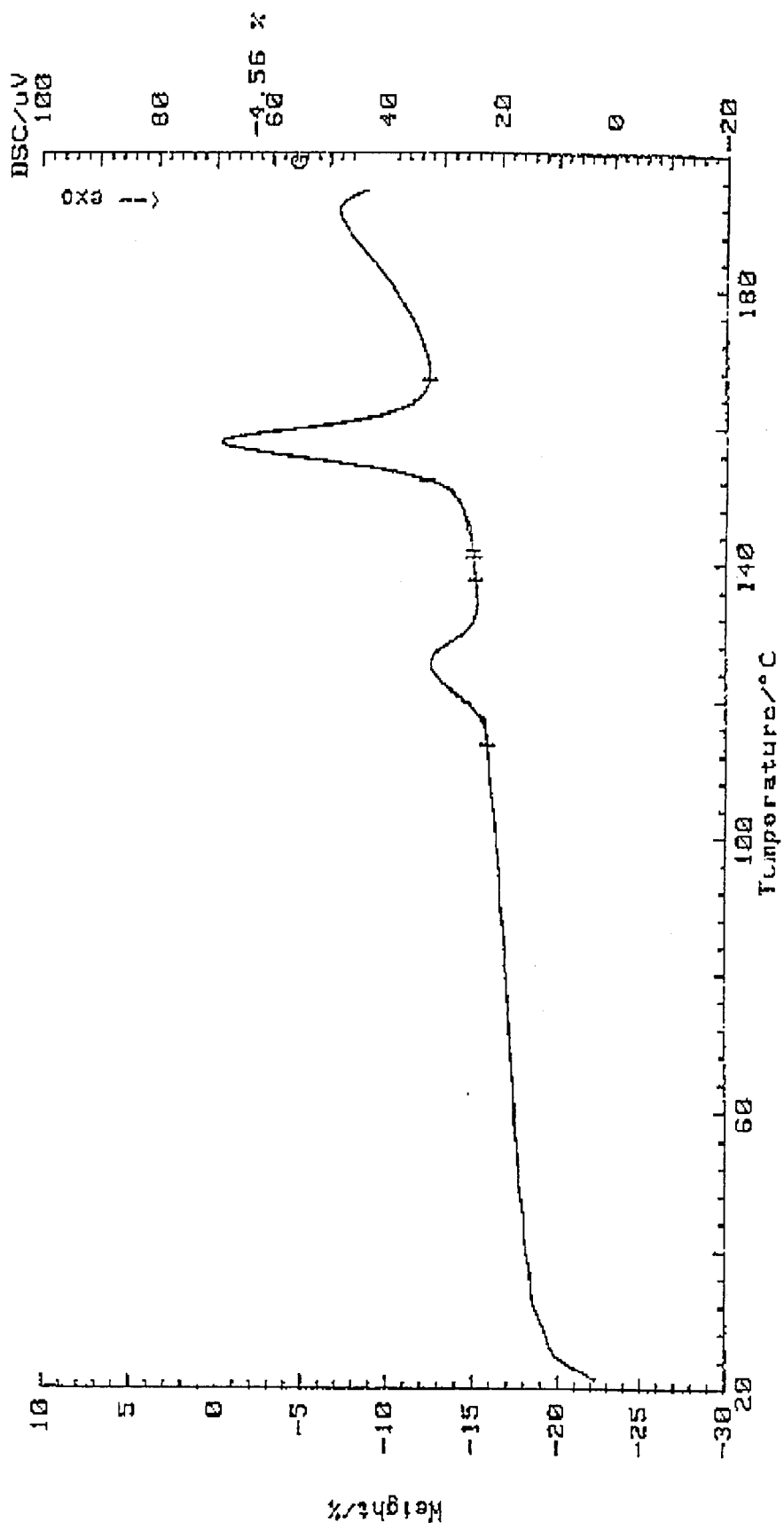
FIG. 8 shows a DSC curve of the molecular complex tegafur-methyluracil in the ratio of 1:2.
Figure 9:
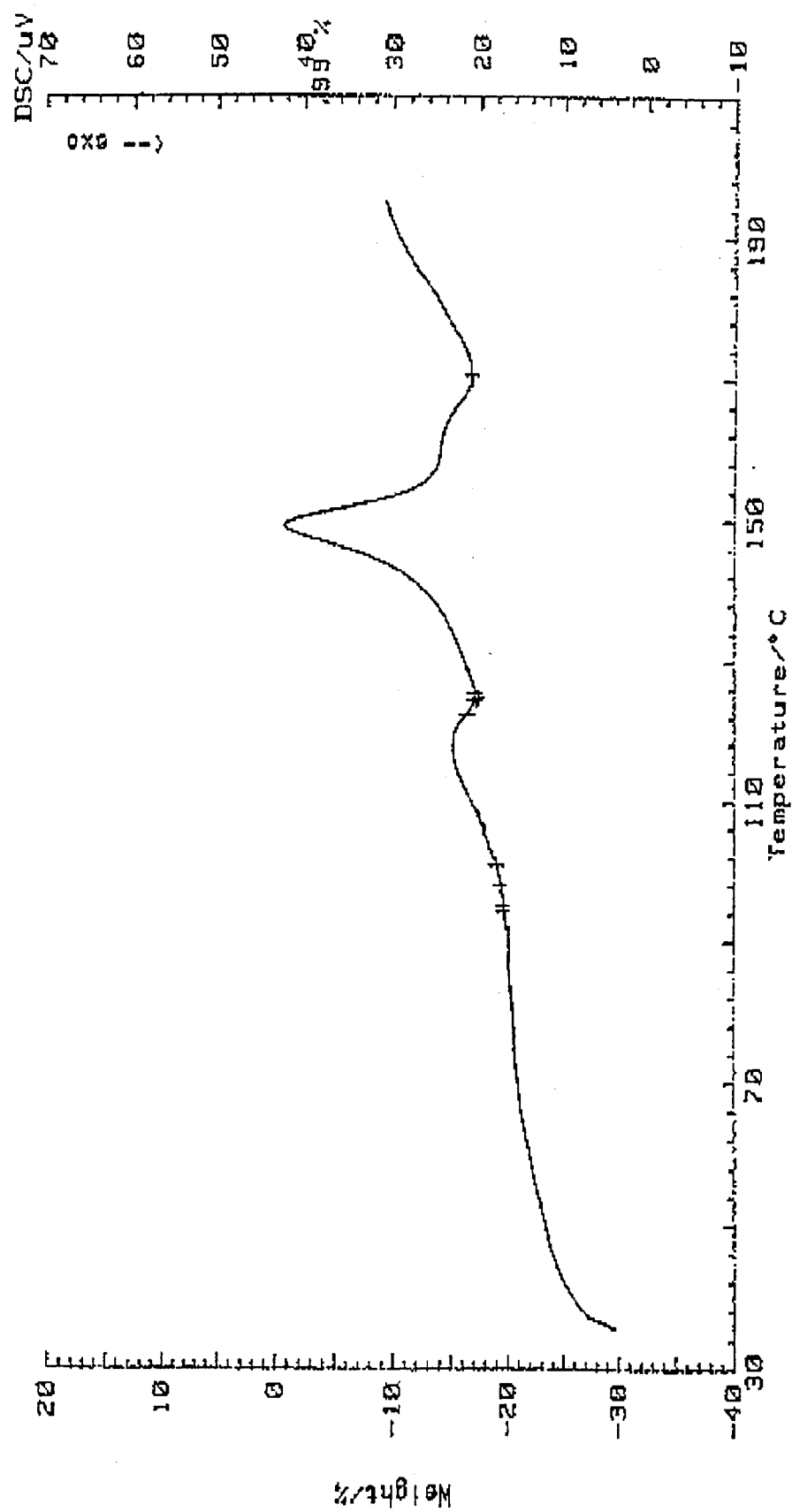
FIG. 9 shows a DSC curve of the complex compound tegafur-licorice.
Figure 10:
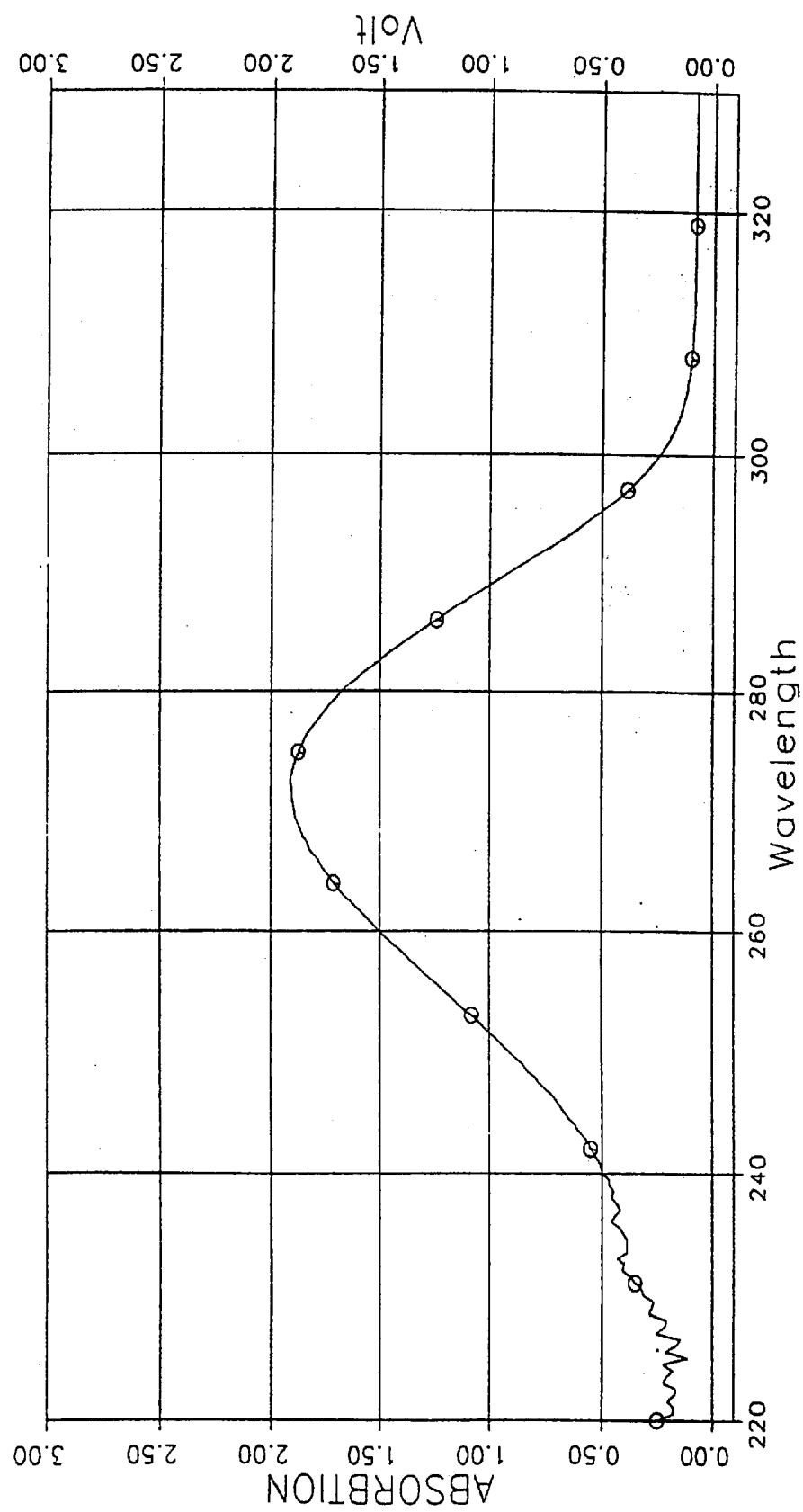
FIG. 10 shows a UV spectrum of the claimed form V of U. tegafur.
Figure 11:
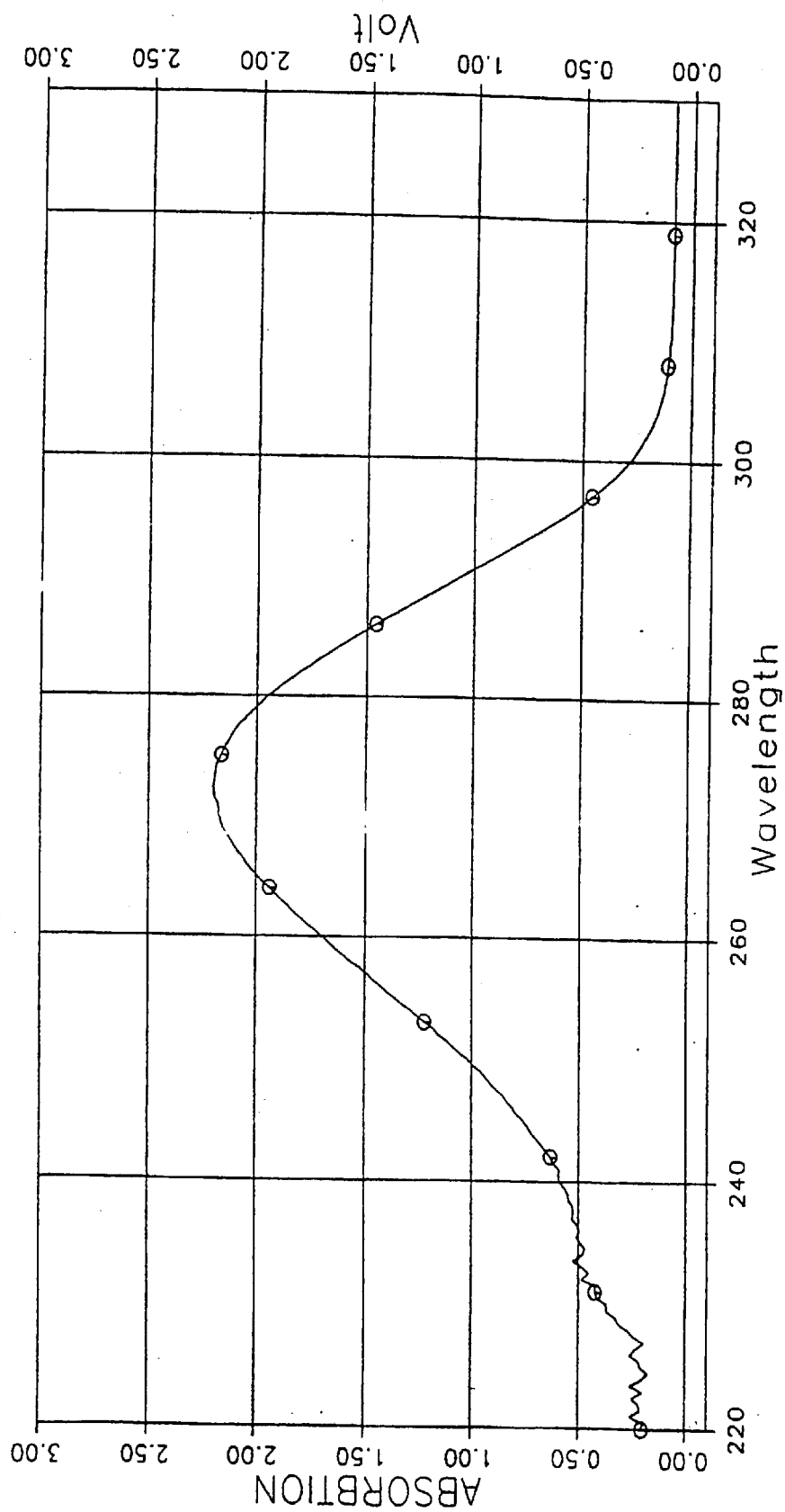
FIG. 11 shows a UV spectrum of pharmacopeial tegafur.
Figure 12:
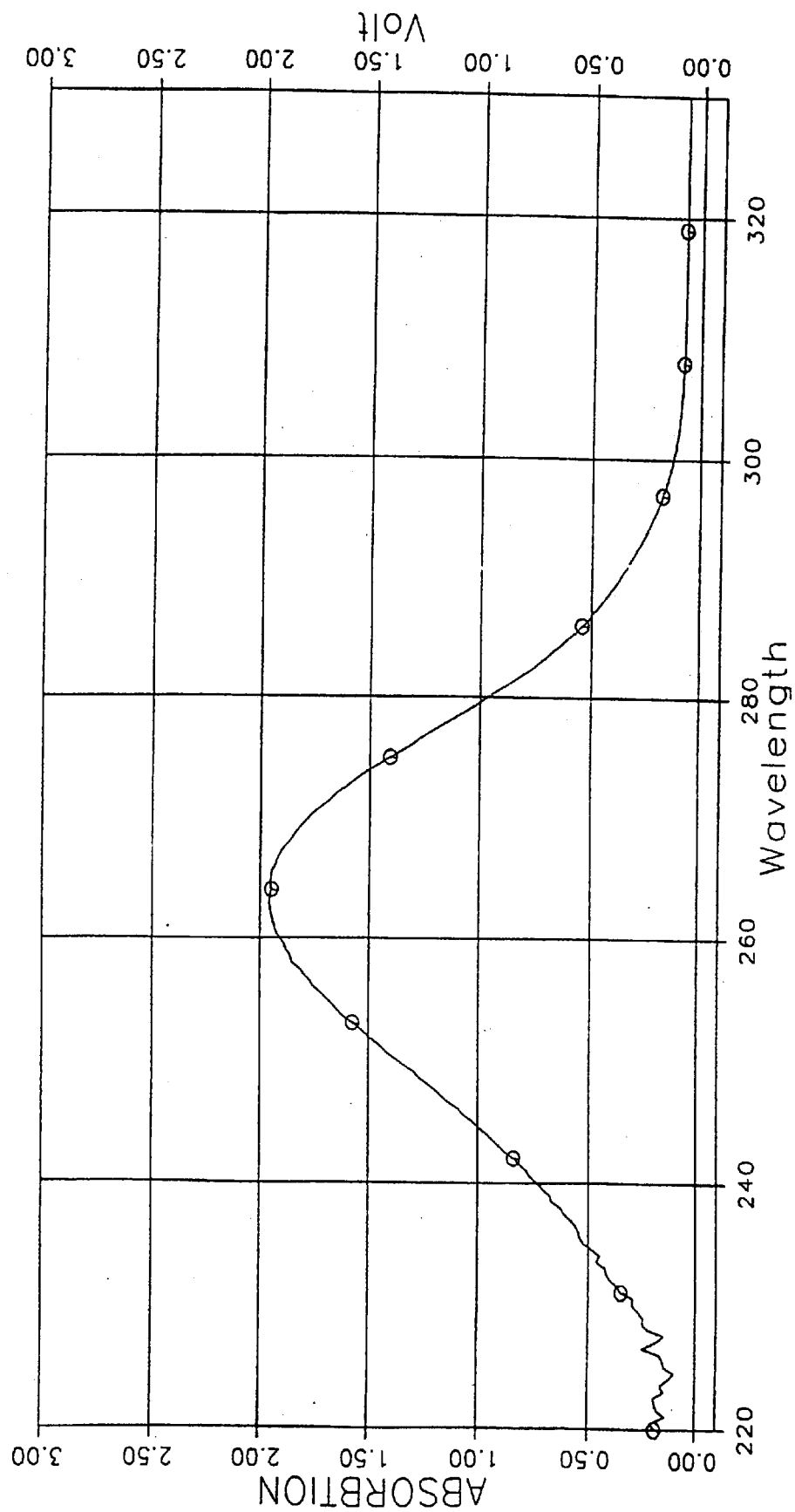
FIG. 12 shows a UV spectrum of the molecular complex tegafur-methyluracil in the ratio of 1:2.
Figure 13:
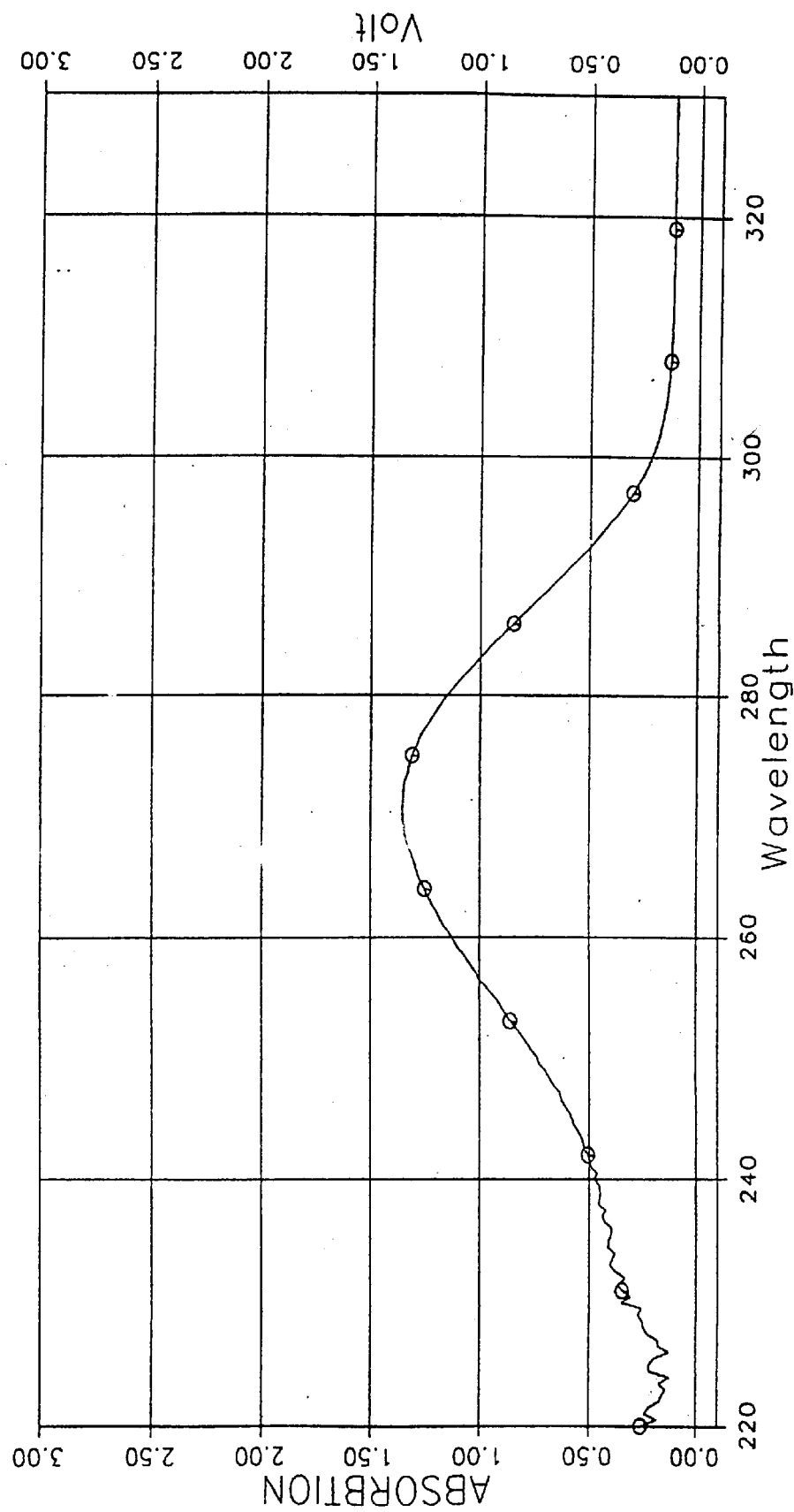
FIG. 13 shows a UV spectrum of the complex compound tegafur-licorice.

The crystalline modification of tegafur according to the present invention is prepared in the following manner.

A saturated aqueous solution of the starting component—pharmacopeial tegafur (corresponds to FS 42-1182-86)—is prepared at the temperature of 45° C. 0.5 liter of the obtained solution is dispersed into a container with chloroform preliminarily cooled down to 2° C. The volume of the chloroform is 0.4 liter. The suspension is allowed to settle, the chloroform layer with the precipitate is separated, the precipitate is filtered-off, the residual solvent is removed at a reduced pressure ($10^{-1}$ mm Hg) to obtain the target product. The yield of form V of tegafur is 62% of the starting pharmacopeial substance.

2. Preparing a Tegafur-Methyluracil Complex (1:2)

0.5 liter of a 0.1 M aqueous solution of form V of tegafur and 0.5 liter of a 0.2 M aqueous solution of Betamecil are prepared at the temperature of 100° C. The resulting solutions are carefully combined and left in a thermostat at the temperature of 60° C. for 1.5 h. Then the solution is cooled down to 2° C., the precipitate is filtered-off and dried at a reduced pressure ($10^{-1}$ mm Hg) to obtain the target product. The yield is 71%.

3. Preparing a Tegafur-Methyluracil Complex (1:1)

0.5 liter of a 0.2 M aqueous solution of form V of tegafur and 0.5 liter of a 0.2 M aqueous solution of methyluracil are prepared at the temperature of 100° C. The resulting solutions are carefully combined and left in a thermostat at the temperature of 60° C. for 3 h. Then the solution is cooled down to 2° C., the precipitate is filtered-off and dried at a reduced pressure ($10^{-1}$ mm Hg) to obtain the target product.

The yield is 68%.

4. Preparing a Complex of Tegafur and a Mixture of Organic Constituents of Licorice Extract As a ligand, dry licorice extract (Radices Glycyrrhizae) is used (S. I. Uspenskaya et al., Rossiiskii Khimicheskii Zhurnal, 1997, vol. 41, No. 5, pp. 124–129). The dry extract comprises an amorphous, porous, hygroscopic powder having a characteristic color and a specific odor. During storage the powder may clump, but the clumps become easily destroyed under shaking. The extract is readily soluble in water and gives opalescing solutions. The content of glycyrrhizic acid in dry licorice extract is 20.12%.

10 g of form V of tegafur are dissolved in 0.25 liter of water at the temperature of 40° C. In another container 5 g of dry licorice extract are dissolved in 0.1 liter of water at the same temperature. The resulting solutions are combined and left in a thermostat at the temperature of 40° C. for 30 minutes. Then the solution is cooled rapidly down to 2° C., the precipitate is filtered-off and dried to obtain the target product. The yield is 75%.

The obtained novel modification of tegafur and the complex compounds based on said modification were investigated by x-ray powder diffraction analysis techniques.

The x-ray powder diffraction analysis was carried out on an automated powder diffractometer (CuK, radiation, graphite monochromator on secondary run; scan mode, 4 to 64 2θ; step, 0.1°; scan rate, 2°/min). The diffraction pattern of the claimed form V and of the complexes with methyluracil displays characteristic reflections. The x-ray powder diffraction pattern of the amorphous complex with licorice was recorded as described above, the only difference being in that, the sample being hygroscopic, recording was carried out under a fine polymeric (Mylar) film. The x-ray powder diffraction pattern of the complex with licorice displays diffuse scattering (amorphous halo), typical of amorphous substances (Whittaker E. J. W., Crystallography, Pergamon Press, Oxford, 1981) in the range of 15–30 2θ°, and a broad reflection of the film polymer with a center in the vicinity of 11 2θ°, superposed thereon.

The results are shown in FIGS. 1–5.

The investigations carried out with the help of differential scanning calorimetry, shown in FIGS. 6–9, prove the novelty of the proposed medicinal compounds. The DSC characteristics of form V differ essentially from both the pharmacopeial sample of tegafur (which corresponds to FS 42-1182-86) and the hitherto-known polymorphic modifications.

Thermoanalytical investigations were carried out on an STA-409 thermoanalyzer (NETZSCH, Germany), which allows carrying out simultaneous investigations by thermogravimetic techniques (TG) and by differential scanning calorimetry techniques (DSC). The investigations were carried out in the atmosphere of dry helium (1 atm) with the scan rate of 10°/min. In the experiments, 7–20 mg weighed samples were placed in platinum crucibles.

The temperature corresponding to the onset of a peak on the DSC curve was determined from the intersection of the straight line corresponding to the datum line and with the straight line which is a tangent at the inflection point of the ascending line of the peak.

To determine the sensitivity coefficients which relate the area under the DSC curve with the thermal effect, a calibration against indium and sapphire was carried out under the conditions identical to those in the working experiments. The integration of peaks on the DSC curves and the calculations of thermal effects were carried out in accordance with programs which are part of the software of the STA-409 instrument.

The UV spectra (FIGS. 10–13) were recorded on an "Aminec" spectrophotometer. Solutions with the concentration of 0.2% were prepared in a 0.1 M phosphate buffer with pH=6.8.

INDUSTRIAL APPLICABILITY

Determination of the Solubility of Investigated Preparations and of Tegafur

The solubility was determined in accordance with the requirements set out in the article "Solubility", USPXXTIII (1995, p. 2071).

TABLE 1

| Description of sample | Temperature of solvent, ° C. | Solubility | | |
|---|---|---|---|---|
| | | g/ml | % | % with respect to tegafur |
| pharmacopeial tegafur | 20 | 0.0080 | 0.8 | |
| Form V of tegafur | 20 | 0.0150 | 1.5 | 187.5 |
| Complex compound 1a | 20 | 0.0095 | 0.95 | 119.0 |
| Complex compound 1b | 20 | 0.0102 | 1.02 | 127.5 |
| Complex compound 2 | 20 | Solubility was not determined, because the preparation forms opalescing solutions | — | |

As is seen from the data presented in Table 1, the solubility of the claimed preparations: of form V of tegafur, complex compound 1a and 1b is higher than the solubility of pharmacopeial tegafur, the solubility of complex compound 2 could not be determined because of the vegetable component—licorice which forms slightly turbid opalescing solutions.

Determination of Specific Activity—Cytotoxicity of Samples of Claimed Prepatrations, Compared with Pharmacopeial Tegafur on a Culture of Uterine Neck Cancer Cells The determination was carried out by following the known procedure (Mosmann N. T., J. Immunology Methods, 1983, vol. 65, 55–63, Carmichel J. et al., Cancer Res., 1987, vol. 47, 936–946) on a culture of uterine neck cancer cells. The cells were grown at 37° C. on the RPMI 1640 medium with additives of a 10%embryonal serum of cows and 200 u/ml of gentamicin. $CO_2$ content in the incubator atmosphere was 10%. The cells which were in the exponential phase of growth were suspended with trypsin and inoculated in an amount of $4 \times 10^3$ into each socket of a 96-socket dish for monolayer cultures. Solutions of samples of the preparations to be investigated were prepared by dissolving 23 mg of each preparation in 10 ml of a culture broth, $10^{-2}$ M solutions being thus obtained. These were starting solutions for obtaining solutions of a lower concentration by diluting them with the culture broth. Directly before adding the solutions to the cells, these solutions were sterilized by filtering through millipore filters. One day after the inoculation of the cells, solutions of samples of the preparations to be investigated in prescribed concentrations were added into each socket of the dish. After that the cells grew for another 4 days.

All in all, 9 concentrations of each of the 4 samples of the investigated preparations were tested.

Quantitative estimation of the cytotoxicity of the investigated preparations was carried out with the use of 3-(4,5-dimethylthiazol-2-yl)-2,5-diphenyltetrazolium bromide (MTT). NTT has a selective ability for metabolizing in cell mitochondria with the formation of formasane, a colored produce which has an absorption maximum at the wavelength of 530–570 nm, there existing a correlation between the degree of the inhibition of mitochondria and the staining of cells. 0.5 mg/ml was added into each socket of the dish 4 hours before the completion of cells cultivation. On completion of the incubation, the culture broth was removed from the dish sockets, the formasane crystals were dissolved, and the cells were scanned on an automatic Multiscan MCC/340P reader at the 540 nm wavelength. The results were calculated in percent of the cells subjected to the effect of the investigated preparations, absorbed at 540 nm, as against the absorption of control cells.

The action of each concentration of the investigated preparations on cancer cells was estimated from the results of 4–6 independent experiments, treated by methods of mathematical statistics. The data obtained in the investigations are presented in Table 2 and in FIG. 14.

TABLE 2

| Concentration of preparations, M (on conversion to tegafur) 1 | Optical density at 540 nm ||||
|---|---|---|---|---|
| | Pharma-copeial tegafur 2 | Form V of tegafur 3 | Complex compound 1a (tegafur and methyl-uracil) 4 | Complex compound (tegafur and licorice) 5 |
| $10^{-6}$ | 0.76 ± 0.05 | 0.79 ± 0.08 | 0.45 ± 0.04 | 0.64 ± 0.04 |
| $5 \times 10^{-6}$ | 0.76 ± 0.08 | 0.73 ± 0.03 | 0.53 ± 0.–3 | 0.96 ± 0.09 |
| $10^{-5}$ | 0.81 ± 0.09 | 0.73 ± 0.08 | 0.38 ± 0.04 | — |
| $5 \times 10^{-5}$ | 0.80 ± 0.10 | 0.70 ± 0.03 | 0.35 ± 0.06 | 0.54 ± 0.08 |
| $10^{-4}$ | 0.81 ± 0.13 | 0.56 ± 0.06 | 0.74 ± 0.12 | 0.45 ± 0.03 |
| $5 \times 10^{-4}$ | 0.56 ± 0.12 | 0.44 ± 0.05 | 0.37 ± 0.05 | 0.30 ± 0.05 |
| $10^{-3}$ | 0.45 ± 0.06 | 0.35 ± 0.02 | 0.32 ± 0.05 | 0.33 ± 0.06 |
| $5 \times 10^{-3}$ | 0.28 ± 0.005 | 0.25 ± 0.02 | 0.16 ± 0.01 | 0.32 ± 0.005 |
| $10^{-2}$ | 0.26 ± 0.04 | 0.16 ± 0.01 | 0.06 ± 0.03 | 0.04 ± 0.005 |

Figure 14:
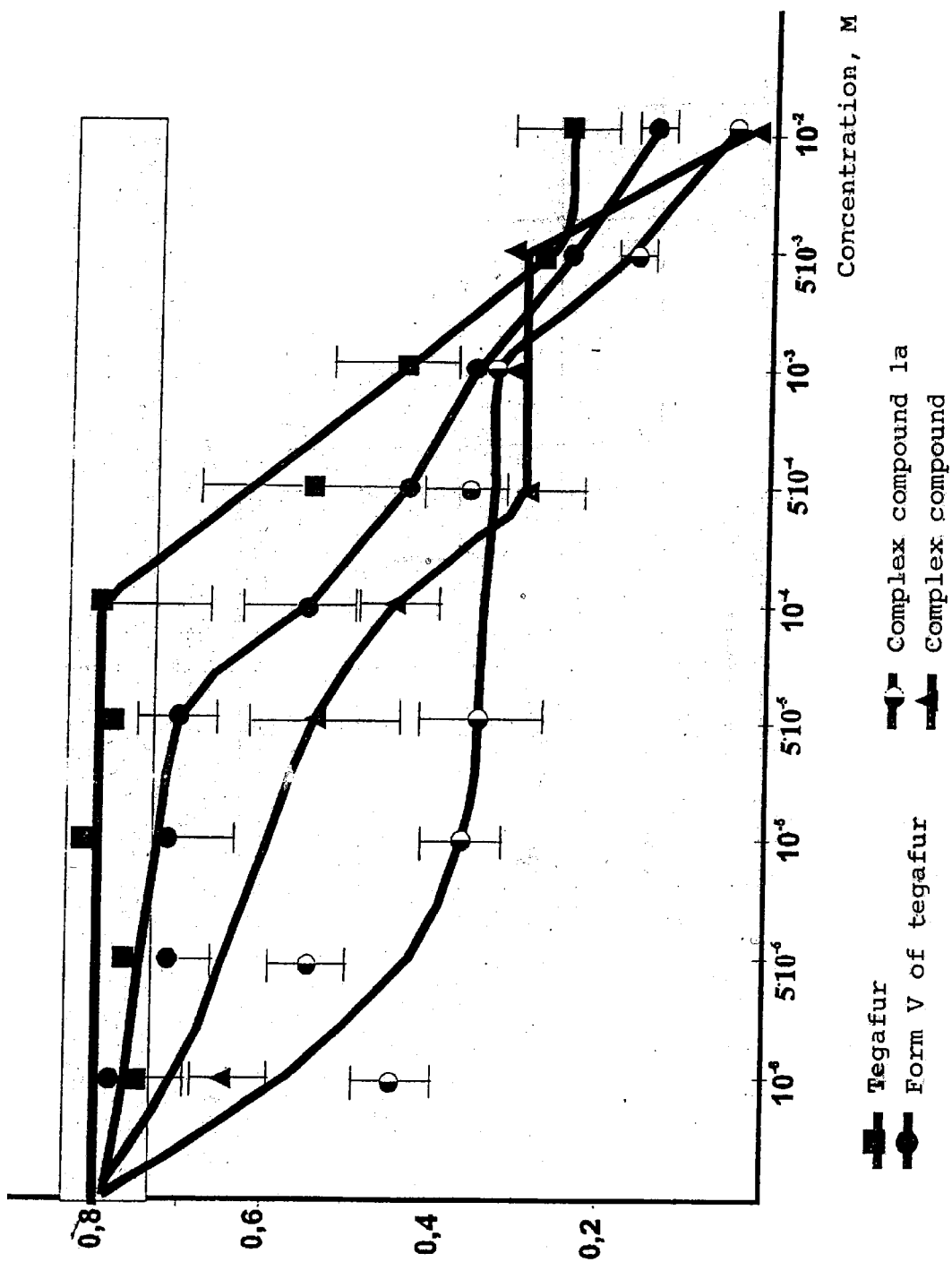
FIG. 14 shows the results of studying the specific activity of pharmacopeial tegafur, of form V of tegafur, of complex compound 1a, and of complex compound 2.

As is seen from the data of Table 2 and from the plot presented in FIG. 14, all the investigated preparations produce different cytotoxic effect on cancer cells. However, the claimed preparations, namely, form V of tegafur, and also complex compounds 1a and 2 excel tegafur essentially in the effect on the proliferation of cancer cells. For instance, tegafur in the range of concentrations of $10^{-6}–10^4$ M does not affect the proliferation of cancer cells. Form V of tegafur inhibits the proliferation of cells at the concentration of $5 \times 10^{-5}$ M; at the concentration of $10^{-4}$ M the preparation inhibits the proliferation by 70% more intensively than tegafur does. Complex compound 1a (tegafur-methyluracil) produces inhibiting is effect on the proliferation of cells already starting with the concentration of $10^{-6}$ M; the same applies to complex compound 2 (tegafur-licorice). It should be taken into account that in complex compound 1a form V of tegafur is present in a ½ smaller amount, and in compound 2 in a ⅓ smaller amount. Hence, a clearly pronounced cytotoxic effect is observed in this case.

What is claimed is:

1. A crystalline modification of 5-fluoro-1-(tetrahydro-2-furyl)uracil, characterized in the x-ray powder diffraction pattern by the following interplanar distances d and the relative intensity of reflections I:

| d, Å | I |
|---|---|
| 9.035 | 63 |
| 7.237 | 23 |
| 6.149 | 19 |
| 5.839 | 100 |
| 5.413 | 17 |
| 4.704 | 42 |
| 4.551 | 62 |
| 4.104 | 36 |
| 4.041 | 28 |
| 3.966 | 25 |
| 3.730 | 20 |
| 3.626 | 25 |
| 3.588 | 42 |
| 3.473 | 60 |
| 3.437 | 50 |
| 3.255 | 30 |
| 3.143 | 36 |
| 2.915 | 23 |
| 2.382 | 16 |
| 2.336 | 20 |

2. A complex compound formed by neutral organic molecules of medicinal substances consisting essentially of 5-fluoro-1-(tetrahydro-2-furyl)uracil and licorice (Radices Glycyrrhizae).

3. A complex compound formed by neutral organic molecules of medicinal substances, consisting essentially of 5-fluoro-1-(tetrahydro-2-furyl)uracil and 2,4-dioxo-6-methyl-1,2,3,4-tetrahydropyrimidine.

4. A complex compound according to claim 3, wherein 2,4-dioxo-6-methyl-1,2,3,4-tetrahydropyrimide is Betamecil.

5. A complex compound according to claim 3, wherein the 5-fluoro-1-(tetrahydro-2-furyl)uracil and 2,4-dioxo-6-methyl-1,2,3,4-tetrahydropyrimidine are present in a 1:2 molar ratio respectively.

6. A complex compound according to claim 5, wherein the x-ray powder diffraction pattern is characterized by the following interplanar distances d and the relative intensity of reflections I:

| d, Å | I |
|---|---|
| 9.090 | 19 |
| 7.234 | 32 |
| 6.883 | 100 |
| 5.864 | 13 |
| 4.831 | 27 |
| 4.571 | 13 |
| 4.197 | 25 |
| 3.627 | 15 |
| 3.448 | 18 |
| 3.254 | 26 |
| 3.192 | 13 |
| 3.149 | 6 |
| 2.933 | 13 |
| 2.448 | 8 |
| 2.300 | 8. |

7. A complex compound according to claim 3, wherein the medicinal substances are present in a 1:1 molar ratio, respectively.

8. A complex compound according to claim 7, wherein the x-ray powder diffraction pattern is characterized by the following interplanar distances d and the relative intensity of the reflections I:

| d, Å  | I   |
|-------|-----|
| 7.187 | 53  |
| 6.841 | 100 |
| 4.806 | 41  |
| 4.181 | 37  |
| 3.669 | 20  |
| 3.474 | 21. |

9. A complex compound formed by neutral organic molecules of medicinal substances, the medicinal substances consisting essentially of 5-fluoro-1-(tetrahydro-2-furyl)uracil and licorice (Radices Glycyrrhizae) in a weight ratio of 1:1 to 4:1.

10. A complex compound according to claim 9, wherein the 5-fluoro-1-(tetrahydro-2-furyl)uracil and the licorice are present in a weight ratio of 2:1, respectively.

11. A complex compound according to claim 10, wherein the clearly pronounced reflections typical of crystalline forms are absent in the x-ray powder diffraction pattern.

12. A complex compound formed by neutral organic molecules of medicinal substances, the medicinal substances consisting essentially of 5-fluoro-1-(tetrahydro-2-furyl)uracil and 2,4-dioxo-6-methyl-1,2,3,4-tetrahydropyrimidine and the 5-fluoro-1-(tetrahydro-2-furyl)uracil is a crystalline modification characterized by an x-ray powder diffraction having the following interplanar distances d and the relative intensity of reflections I:

| d, Å  | I   |
|-------|-----|
| 9.035 | 63  |
| 7.237 | 23  |
| 6.149 | 19  |
| 5.839 | 100 |
| 5.413 | 17  |
| 4.704 | 42  |
| 4.551 | 62  |
| 4.104 | 36  |
| 4.041 | 28  |
| 3.966 | 25  |
| 3.730 | 20  |
| 3.626 | 25  |
| 3.588 | 42  |
| 3.473 | 60  |
| 3.437 | 50  |
| 3.255 | 30  |
| 3.143 | 36  |
| 2.915 | 23  |
| 2.382 | 16  |
| 2.336 | 20  |

13. A complex compound according to claim 12, wherein the medicinal substances are present in a 1:2 molar ratio, respectively.

14. A complex compound according to claim 4, wherein the medicinal substances are present in a 1:1 molar ratio, respectively.

* * * * *